United States Patent
Vidal et al.

(10) Patent No.: US 6,210,447 B1
(45) Date of Patent: Apr. 3, 2001

(54) COMPOSITIONS CONTAINING PYRAZOLIN-3,5-DIONE COUPLERS FOR USE IN KERATIN FIBER DYEING METHODS AND KITS

(75) Inventors: Laurent Vidal, Paris; Gërard Malle, Villiers sur Morin, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/155,192

(22) PCT Filed: Mar. 21, 1997

(86) PCT No.: PCT/FR97/00509

§ 371 Date: Feb. 10, 1999

§ 102(e) Date: Feb. 10, 1999

(87) PCT Pub. No.: WO97/35553

PCT Pub. Date: Oct. 2, 1997

(30) Foreign Application Priority Data

Mar. 22, 1996 (FR) .................................................. 96 03630

(51) Int. Cl.$^7$ ...................................................... A61K 7/13
(52) U.S. Cl. ........................................ 8/409; 8/423; 8/573
(58) Field of Search ................................ 8/407, 409, 423, 8/573; 548/366.4

(56) References Cited

U.S. PATENT DOCUMENTS

| | | | |
|---|---|---|---|
| 2,427,911 | * 9/1947 | Kendall et al. | 548/366.4 |
| 2,439,098 | * 4/1948 | Porter et al. | 548/366.4 |
| 3,061,432 | 10/1962 | Menzel et al. | 430/376 |
| 3,227,554 | 1/1966 | Barr et al. | 430/382 |
| 3,379,533 | * 4/1968 | Jenkins et al. | 548/366.4 |
| 3,419,391 | 12/1968 | Young | 430/387 |
| 3,725,067 | 4/1973 | Bailey et al. | 430/476 |
| 3,820,948 | 6/1974 | Berth | 8/409 |
| 3,926,631 | 12/1975 | Arai et al. | 430/226 |
| 4,128,425 | 12/1978 | Greenwald | 430/440 |
| 4,293,543 | 10/1981 | Cotte et al. | 424/59 |
| 4,500,630 | 2/1985 | Sato et al. | 430/386 |
| 5,256,526 | 10/1993 | Suzuki et al. | 430/384 |
| 5,441,863 | 8/1995 | Tang et al. | 430/558 |
| 5,457,210 | 10/1995 | Kim et al. | 548/262.4 |

FOREIGN PATENT DOCUMENTS

| | | |
|---|---|---|
| 2 160 317 | 6/1973 | (DE) . |
| 2 359 999 | 6/1975 | (DE) . |
| 3 731 395 | 4/1989 | (DE) . |
| 3 843 892 | 6/1990 | (DE) . |
| 4 009 097 | 9/1991 | (DE) . |
| 4 133 957 | 4/1993 | (DE) . |
| 0 030 680 | 6/1981 | (EP) . |
| 0 119 860 | 9/1984 | (EP) . |
| 0 285 274 | 10/1988 | (EP) . |
| 0 304 001 | 2/1989 | (EP) . |
| 0 309 652 | 4/1989 | (EP) . |
| 0 320 764 | 6/1989 | (EP) . |
| 0 456 226 | 11/1991 | (EP) . |
| 0 488 248 | 6/1992 | (EP) . |
| 0 488 909 | 6/1992 | (EP) . |
| 0 518 238 | 12/1992 | (EP) . |
| 0 547 864 | 6/1993 | (EP) . |
| 0 557 851 | 9/1993 | (EP) . |
| 0 578 248 | 1/1994 | (EP) . |
| 0 591 103 | 4/1994 | (EP) . |
| 1 564 999 | 4/1969 | (FR) . |
| 2 075 583 | 10/1971 | (FR) . |
| 2 466 492 | 4/1981 | (FR) . |
| 2 586 913 | 3/1987 | (FR) . |
| 1 026 978 | 3/1963 | (GB) . |
| 1 153 196 | 6/1966 | (GB) . |
| 1 458 377 | 9/1974 | (GB) . |
| 58-42045 | 3/1983 | (JP) . |
| 59-99437 | 6/1984 | (JP) . |
| 59-162548 | 9/1984 | (JP) . |
| 59-171956 | 9/1984 | (JP) . |
| 60-33552 | 2/1985 | (JP) . |
| 60-43659 | 3/1985 | (JP) . |
| 60-172982 | 9/1985 | (JP) . |
| 60-190779 | 9/1985 | (JP) . |
| 62-79337 | 12/1987 | (JP) . |
| 63-169571 | 7/1988 | (JP) . |
| 62 36011 | 8/1994 | (JP) . |
| 70 36159 | 2/1995 | (JP) . |
| 70 84348 | 3/1995 | (JP) . |
| 70 92632 | 4/1995 | (JP) . |
| WO 92/04349 | 3/1992 | (WO) . |
| WO 92/04883 | 4/1992 | (WO) . |
| WO 94/04130 | 3/1994 | (WO) . |
| WO 94/08959 | 4/1994 | (WO) . |
| WO 94/08969 | 4/1994 | (WO) . |
| WO 94/08970 | 4/1994 | (WO) . |

OTHER PUBLICATIONS

English language translation of JP 7–84348, Konica Corp, pp. 1–35, Mar. 1995.*

(List continued on next page.)

*Primary Examiner*—Caroline D. Liott
(74) *Attorney, Agent, or Firm*—Finnegan, Henderson, Farabow, Garrett & Dunner, L.L.P.

(57) ABSTRACT

The present invention relates to a composition for dyeing keratin fibers, in particular human hair, containing, in a medium which is suitable for dyeing:

as coupler, at least one compound of formula:

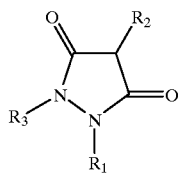

(I)

or one of the addition salts thereof with an acid;
and at least one oxidation base.

9 Claims, No Drawings

OTHER PUBLICATIONS

English language translation of JP 7–36,159, Konica Corp, pp. 1–50, Feb. 1995.*

R. Stollé, "Ueber die Ueberführung der secundären Säurehydrazide in Derivate des Furodiazols, Pyrrodiazols und Thiodiazols", Chemischen Gesellschaft, pp. 797–798, 1899.

Hans Beyer et al., "Über die Pyrazolbildung aus α–Chlor–acetessigester und Thiocarbohydazid", Chemische Berichte, pp. 2550–2555, 1956.

H. Wilde et al., Synthese von 4H–Pyrazolo[1,5–a]benzimidazolen, Journal Für Praktische Chemie, pp. 829–836, 1984.

Lidia Wyzgowska et al., "O Reakcjach Trikarboetoksymetanu VIII", Acta Poloniae Pharmaceutica, pp. 83–88, 1982.

E. Hannig et al., "Zur Kenntnis des 4–aminierten Phenylbutazons", Die Pharmazie, pp. 231, Apr., 1980.

Giuliana Cardillo et al., "Su due constituenti minori della Kamala", Gazetta Chimica Italiana, pp. 725–734, Feb., 1965.

Thomas Kauffman et al., Synthese von Amidrazonon aus Nitrilen und Natriumhydrazid, pp. 3436–3443, Dec., 1964.

von Helmut Dorn et al., "Synthese und Methylierung von 1H–Pyrazolo[3,4–b]pyrazinen, einer neuen Klasse von Purin–Antagonisten", Annalen der Chemie, pp. 118–123, 1968, No month available.

von Helmut Dorn et al., "Über die elektrophile Substitution von 3(5)–Amino–pyrazol", Annalen der Chemie, pp. 141–146, 1967, No month available.

Mohamed Helmi Elnagdi et al., "Studies on 3,5–pyrazolidinediones. IV. Addition of 4–Arylazo–3,5–pyrazolidinediones to Ethyl Acrylate", Bulletin of Them Chemical Society of Japan, vol. 46, pp. 1830–1833, Jun., 1973.

Günther Ege et al., "A Simple Synthesis of 3(5)–Aminopyrazole", Angew. Chem. internat. Edit, vol. 13, No. 3, pp. 206–207, Mar., 1974.

Kazumasa Takahashi et al., "Syntheses of 3(5)–Substituted–4–(N–methylanilino)–5(3)–aminopyrazoles by Reaction of β–Hydroxy–α–cyano–enamines with Hydrazines", Journal of Synthetic Organic Chemistry, No. 8, pp. 794–796, Aug., 1985.

Chiara B. Vincentini et al., "Pyrazolo[3,4–d][1,2,3] Triazole–1–carboxamides and 5–Alkylaminopyrazolo[3,4–d]oxazoles: Synthesis and Evaluation of the in Vitro Antifungal Activity", Il Farmaco, Vo. 47, No. 7, 8, pp. 1021–1034, Aug., 1992.

Edward C. Taylor et al., "The Reaction of Malononitrile with Substituted Hydrazines: New Routes to 4–Aminopyrazolo[3,4–d]pyrimidines", Journal of the merican Chemical Society, vol. 81, No. 10, pp. 2456–2464, May, 1959.

C.B. Vincentini et al., "A New Fused Heterocyclic System: 6H–Pyrazolo[3,4–c][1,2,5]thiadizine 2,2–Dioxide", Journal of Heterocyclic Chemistry, vol. 26, No. 3, pp. 797–803, Jun., 1989.

E.J. Browne et al., "Triazoles. Part VII. Syntheses of Substituted 1,2,4–Triazoles", Journal of The Chemical Society, pp. 5149–5152, Oct., 1962.

Philip Magnus et al., "Synthesis of helical Poly–β–pyrroles. Multiple Atropisomerism Resulting in Helical Enantiomorphic Conformations", Journal of the American Chemical Society, vol. 112, No. 6, pp. 2465–2468, Mar., 1990.

Paul Carter et al., "Studies on the Synthesis of the Antitumor Agent CC–1065. Synthesis of PDE I and PDE II, Inhibitors of Cyclic Adenosine–3',5'–monophosphate Phosphodiesterase Using the 3,3'–Bipyrrole Strategy", Journal of the American Chemical Society, vol. 109, No. 9, pp. 2711–2717, Apr., 1987.

H. Koopman, "Investigations on Herbicides IV, The synthesis of 2,6–dichlorobenzonitrile", Recueil, vol. 80, No. 9–10, pp. 1075–1083, Oct., 1961.

Joseph Bailey, "Synthesis of 1H–Pyrazolo[3,2–c]–s–Triazoles and Derived Azamethine Dyes", Journal of the Chemical Society, pp. 2047–2052, 1977, No month available.

Mohamed Helmy Elnagdi et al., "Routes for the Synthesis of 3,5–Diaminopyrazoles, 2–Aminopyrazolo[1,5–a]pyrimidines and 5–Aminopyrazolo[1,5–a]pyramidines", Journal f. prakt. chemie, Band 320, heft 4, pp. 533–538, 1978.

* cited by examiner

COMPOSITIONS CONTAINING PYRAZOLIN-3,5-DIONE COUPLERS FOR USE IN KERATIN FIBER DYEING METHODS AND KITS

The invention relates to a composition for the oxidation dyeing of keratin fibres, in particular human hair, containing at least one pyrazoline-3,5-dione compound as coupler and at least one oxidation base.

It is known to dye keratin fibres, and in particular human hair, with dye compositions containing oxidation dye precursors, in particular ortho- or para-phenylene diamines, ortho- or para-aminophenols, and heterocyclic compounds, which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is known that the shades obtained with these oxidation bases can be varied by combining them with couplers or colour modifiers, the latter being chosen in particular from aromatic meta-diamines, meta-aminophenols, meta-diphenols and certain heterocyclic compounds such as indole compounds.

The variety of molecules used as oxidation bases and couplers allows a wide range of colours to be obtained.

The so-called "permanent" coloration obtained by means of these oxidation dyes must moreover satisfy a certain number of requirements. Thus, it must have no toxicological drawbacks it must allow shades to be obtained in the desired intensity and it must show good resistance to external agents (light, bad weather, washing, permanent-waving, perspiration, rubbing).

The dyes must also be able to cover grey hair and, lastly, they must be as unselective as possible, i.e. they must allow only the smallest possible colour differences to be obtained along the length of the same keratin fibre, which may, indeed, be differently sensitized (i.e. damaged) between its tip and its root.

The Applicant has now discovered that it is possible to obtain novel, powerful, unselective and particularly resistant dyes, which are capable of giving rise to intense colorations in varied shades, by using pyrazoline-3,5-dione compounds as couplers in the presence of an oxidation base.

This discovery forms the basis of the present invention.

The subject of the invention is a composition for dyeing keratin fibres, and in particular human keratin fibres such as the hair, characterized in that it comprises, in a medium which is suitable for dyeing:

as coupler, at least one pyrazoline-3,5-dione compound of formula (I), or one of the addition salts thereof with an acid:

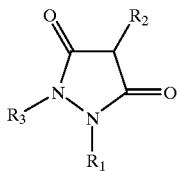

(I)

in which:

$R_2$ represents: a hydrogen atom; a halogen atom such as bromine, chlorine or fluorine; an acetylamido group; an alkoxy radical (such as, for example: methoxy, ethoxy, propyloxy, benzyloxy, methoxyethoxy, phenoxyethoxy, 2-cyanoethoxy, phenethyloxy, p-chlorobenzyloxy, methoxyethylcarbamoylmethoxy); an aryloxy radical (such as, for example: phenoxy, 4-methoxyphenoxy, 4-nitrophenoxy, 4-cyanophenoxy, 4-methanesulphonamidophenoxy, 4-methanesulphonylphenoxy, 3-methylphenoxy, 1-naphthyloxy); an acyloxy radical (such as, for example: acetoxy, propanoyloxy, benzoyloxy, 2,4-dichlorobenzoyloxy, ethoxyalkyloxy, pyruvyloyloxy, cinnamoyloxy, myristoyloxy); an arythio radical (such as, for example: phenylthio, 4-carboxyphenylthio, 2-ethoxy-5-tert-butylphenylthio, 2-carboxyphenylthio, 4-methanesulphonylphenylthio); an alkylthio radical (such as, for example: methylthio, ethylthio, propylthio, butylthio, 2-cyanoethylthio, benzylthio, phenethylthio, 2-(diethylamino)ethylthio, ethoxyethylthio, phenoxyethylthio); a heteroarylthio radical (such as, for example: 5-phenyl-2,3,4,5-tetrazolylthio, 2-benzothiazolylthio); a heteroaryloxy radical (such as, for example: 5-phenyl-2,3,4,5-tetrazolyloxy, 2-benzothiazolyloxy); a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical, an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1,2-dihydro-1-pyridyl radical; an alkylamindo; an arylamido; a radical $NR^{III}R^{IV}$ with $R^{III}$ and $R^{IV}$, which may be identical or different, representing a $C_1$–$C_4$ alkyl, a hydroxyalkyl; a carboxyl; or an alkoxycarboxylic radical; $R_1$ and $R_3$ represent a hydrogen atom; a linear or branched $C_1$–$C_5$ alkyl radical; a $C_2$–$C_4$ mono- or polyhydroxyalkyl radical; a $C_2$–$C_4$ aminoalkyl radical; a phenyl radical; a phenyl radical substituted with a halogen atom or a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy or amino radical; or a radical

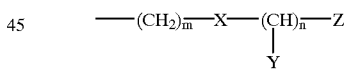

in which m and n are integers, which may be identical or different, between 1 and 3 inclusive, X represents an oxygen atom or an NH group, Y represents a hydrogen atom or a methyl radical, and Z represents a methyl radical, a group OR or NRR' in which R and R', which may be identical or different, denote a hydrogen atom, a methyl radical or an ethyl radical; an amino radical; a $C_1$–$C_4$ alkylamino; a carboxyl radical; an alkoxycarbonyl radical; an aryloxycarbonyl radical; a 5- or 6-membered heterocycle with at least one nitrogen, sulphur or oxygen atom (such as pyridyl, quinolyl, pyrrolyl, morpholyl, furyl, pyrazolyl, triazolyl, tetrazolyl, thiazolyl, oxazolyl, imidazolyl, thiadiazolyl); an acyl radical; a sulphonyl group; a phosphonyl group;

it being understood that when $R_2$ and $R_3$ simultaneously represent a hydrogen atom, then $R_1$ is other than a hydrogen atom, a $C_1$–$C_5$ alkyl radical or a phenyl radical;

and at least one oxidation base.

The addition salts with an acid for the compounds of the invention can be chosen in particular from hydrochlorides, hydrobromides, tartrates, tosylates, benzenesulphonates, sulphates, lactates and acetates.

Among the radicals $R_2$ formula (I) defined above, the preferred radicals are chosen from the group consisting of:

a hydrogen atom; a $C_1$–$C_4$ alkoxy; phenoxy; phenoxy substituted with a halogen atom, a $C_1$–$C_4$ alkyl, a carboxyl, a trifluoromethyl group; an acyloxy radical; benzyloxy; $C_1$–$C_4$ alkylthio; phenylthio; phenylthio substituted with a halogen atom, a $C_1$–$C_4$ alkyl, a carboxyl, a trifluoromethyl group; a $C_1$–$C_4$ alkylamido; phenylamido; a radical $NR'''R^{IV}$ with $R'''$ and $R^{IV}$, which may be identical or different, representing a $C_1$–$C_4$ alkyl, a $C_1$–$C_4$ hydroxyalkyl; a carboxyl; a $C_1$–$C_4$ alkoxycarboxylic radical.

Among the radicals $R_2$ of formula (I) defined above, the radicals more particularly preferred are chosen from the group consisting of: hydrogen; chlorine or bromine; methoxy or ethoxy; phenoxy; 4-methylphenoxy; acyloxy; benzyloxy; methylthio or ethylthio; phenylthio; 4-methylphenylthio; 2-tert-butylphenylthio; acetamido; phenylacetamido; dimethylamino; diethylamino; ethylmethylamino; (β-hydroxyethyl)methylamino.

Even more particularly, the preferred radicals $R_2$ are chosen from the group consisting of: hydrogen; chlorine; ethoxy; phenoxy; benzyloxy; acyloxy; acetamido; dimethylamino.

Among the radicals $R_1$ and $R_3$ of formula (I) defined above, the preferred radicals are chosen from the group consisting of: hydrogen; $C_1$–$C_4$ alkyl (such as methyl, ethyl, isopropyl, t-butyl, n-propyl); $C_2$–$C_4$ mono- or polyhydroxyalkyl (such as 2-hydroxyethyl, 3,4-dihydroxybutyl); $C_2$–$C_4$ aminoalkyl (such as 2-aminoethyl); dialkylaminoalkyl (such as 2-(N,N-dimethylamino)ethyl); pheny; phenyl substituted with a chlorine atom or a methoxy, nitro, trifluoromethyl, amino, methylamino or methyl radical; benzyl; benzyl substituted with a chlorine, a methoxy or a methyl; alkoxycarbonyl (such as methoxycarbonyl, ethoxycarbonyl); aryloxycarbonyl (such as phenyloxycarbonyl); pyridyl; furyl; thienyl; pyrrolyl; thiazolyl; acyl (such as acetyl, 2-ethylcarbonyl).

Among the radicals $R_1$ and $R_3$, the radicals more particularly preferred are chosen from the group consisting of: hydrogen; methyl; ethyl; isopropyl; 2-hydroxyethyl; 2-aminoethyl; phenyl; 2-, 3- or 4-chlropheny; 3- or 4-methoxypheny; benzyl; 3- or 4-toluyl; methoxycarbonyl; ethoxycarbonyl; pyridyl; pyrazolyl; pyrrolyl.

Even more particularly, the preferred radicals $R_1$ and $R_3$ are chosen from the group consisting of:

hydrogen; methyl; ethyl; isopropyl; phenyl; 4-chlorophenyl; 4-toluyl; benzyl; pyridyl; pyrazolyl.

The compounds of formula (I) more particularly preferred are those for which:

$R_1$ denotes hydrogen, methyl, ethyl or phenyl;
$R_2$ denotes chlorine or ethoxy;
$R_3$ denotes methyl, ethyl or phenyl.

As compounds of formula (I) above, mention may be made most particularly of:

1,2-diphenylpyrazoline-3,5-dione,
1,2-diethylpyrazoline-3,5-dione,
1,2-dimethylpyrazoline-3,5-dione,
4-chloro-1,2-diethylpyrazoline-3,5-dione, and the addition salts thereof with an acid.

The pyrazoline-3,5-dione compounds of the invention, their synthetic intermediates and processes for their preparation are described in the patents and patent applications JP 07-036,159, JP 07-084,348 and U.S. Pat. No. 4,128,425, and in the following publications:

L. Wyzgowska, Acta. Pol. Pharm. 1982, 39 (1–3), 83.
E. Hanning, Pharmazie, 1980, 35 (4), 231
M. H. Elnagdi, Bull. Chem. Soc. Jap., 46 (6), 1830, 1973
G. Cardillo, Gazz. Chim. Ital. 1966, 95, (8–9), 973.

The compound(s) of formula (I) preferably represent(s) from 0.0005 to 12% by weight approximately relative to the total weight of the dye composition, and even more preferably from 0.005 to 6% by weight approximately relative to this weight.

The nature of the oxidation bases(s) which can be used in the dye composition according to the invention is not critical. This or these oxidation bases is (are) preferably chosen from para-phenylenediamines, bis(phenyl) alkylenediamines, para-aminophenols, ortho-aminophenols and heterocyclic bases, and the addition salts thereof with an acid.

Among the para-phenylenediamines which can be used as oxidation bases in the dye composition according to the invention, mention may be made in particular of the compounds corresponding to formula (II) below, and the addition salts thereof with an acid:

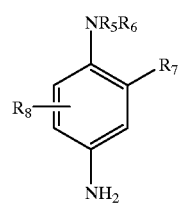

(II)

in which:

$R_5$ represents a hydrogen atom, a $C_1$–$C_4$ alkyl, $C_1$–$C_4$ monohydroxyalkyl, $C_2$–$C_4$ polyhydroxyalkyl or ($C_1$–$C_4$) alkoxy($C_1$–$C_4$)alkyl radical, $R_6$ represents a hydrogen atom or a $C_1$–$C_4$alkyl, $C_1$–$C_4$ monohydroxyalkyl or $C_2$–$C_4$ polyhydroxyalkyl radical, $R_7$ represents a hydrogen atom, a halogen atom such as a chlorine atom, or a $C_1$–$C_4$ alkyl, sulpho, carboxyl, $C_1$–$C_4$ monohydroxyalkyl or $C_1$–$C_4$ hydroxyalkoxy radical, $R_8$ represents a hydrogen atom or a $C_1$–$C_4$ alkyl radical.

In formula (II) above, when $R_7$ is other than a hydrogen atom, then $R_5$ and $R_6$ preferably represent a hydrogen atom and $R_7$ is preferably identical to $R_8$, and when $R_7$ represents a halogen atom, then $R_5$, $R_6$ and $R_8$ preferably represent a hydrogen atom.

Among the para-phenylenediamines of formula (II) above, mention may be made more particularly of para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-(β-methoxyethyl) aminobenzene and 2-chloro-para-phenylenediamine, and the addition salts thereof with an acid.

Among the bis(phenyl)alkylenediamines which can be used as oxidation bases in the dye composition according to the invention, mention may be made in particular of the compounds corresponding to formula (III) below, and the addition salts thereof with an acid:

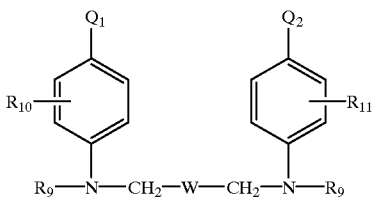

(III)

in which:

$Q_1$ and $Q_2$, which may be identical or different, represent a hydroxyl radical or a radical $NHR_{12}$ in which $R_{12}$ represents a hydrogen atom or a $C_1$–$C_4$ alkyl radical, $R_9$ represents a hydrogen atom or a $C_1$–$C_4$ alkyl, $C_1$–$C_4$ monohydroxyalkyl, $C_2$–$C_4$ polyhydroxyalkyl or $C_1$–$C_4$ aminoalkyl radical in which the amino residue may be substituted, $R_{10}$ and $R_{11}$, which may be identical or different, represent a hydrogen or halogen atom or a $C_1$–$C_4$ alkyl radical, W represents a radical taken from the group consisting of the following radicals

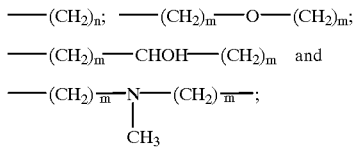

in which n is an integer between 0 and 8 inclusive and m is an integer between 0 and 4 inclusive.

Among the bis(phenyl)alkylenediamines of formula (III) above, mention may be made more particularly of N,N'-bis(β-hydroxyethyl-N,N'-bis-(4'-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition salts thereof with an acid.

Among these bis(phenyl)alkylenediamines of formula (III), N,N'-bis(β-hydroxyethyl)-N,N'-bis(4'-aminophenyl)-1,3-diaminopropanol or one of the addition salts thereof with an acid is particularly preferred.

Among the para-aminophenols which can be used as oxidation bases in the dye composition according to the invention, mention may be made in particular of the compounds corresponding to formula (IV) below, and the addition salts thereof with an acid:

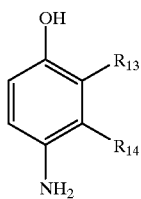

(IV)

in which:

$R_{13}$ represents a hydrogen atom or a $C_1$–$C_4$ alkyl, $C_1$–$C_4$ monohydroxyalkyl, $(C_1$–$C_4)$alkoxy$(C_1$–$C_4)$alkyl or $C_1$–$C_4$ aminoalky radical, $R_{14}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, cyano$(C_1$–$C_4)$alkyl or $(C_1$–$C_4)$alkoxy$(C_1$–$C_4)$alkyl radical, it being understood that at least one of the radicals $R_{13}$ or $R_{14}$ represents a hydrogen atom.

Among the para-aminophenols of formula (IV) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which can be used as oxidation bases in the dye composition according to the invention, mention may be made in particular of 2-aminophenol, 2-amino-1-hydroxy-5-methylbenzene, 2-amino-1-hydroxy-6-methylbenzene and 5-acetamido-2-aminophenol, and the addition salts thereof with an acid.

Among the heterocyclic bases which can be used as oxidation bases in the dye composition according to the invention, mention may be made in particular of pyridine derivatives, pyrimidine derivatives and pyrazole derivatives, and the addition salts thereof with an acid.

Among the pyridine derivatives, mention may be made more particularly of the compounds described, for example, in GB patents 1,026,978 and 1,153,196, such as 2,5-diaminopyridine, and the addition salts thereof with an acid.

Among the pyrimidine derivatives, mention may be made more particularly of compounds described, for example, in German patent DE 2,359,399 or Japanese patents JP 88-169,571 and JP 91-333,495, such as 2,4,5,6-tetraaminopyrimidine and 4-hydroxy-2,5,6-triaminopyrimidine, and the addition salts thereof with an acid.

Among the pyrazole derivatives, mention may be made more particularly of the compounds described in patents DE 3,843,892 and DE 4,133,957 and patent applications WO 94/08969 and WO 94/08970, such as 4,5-diamino-1-methylpyrazole and 3,4-diaminopyrazole, and 1-(4'-chlorobenzyl)-4,5-diaminopyrazole, and the addition salts thereof with an acid.

According to the invention, the oxidation bases(s) preferably represent(s) from 0.0005 to 12% by weight approximately relative to the total weight of the dye composition, and even more preferably from 0.005 to 6% by weight approximately relative to this weight.

The dye composition according to the invention can also contain one or more additional couplers other than the compounds of formula (I) and/or one or more direct dyes, so as to vary the shades obtained with the oxidation bases or the enrich the shades with glints.

The additional couplers which can be used in the composition according to the invention can be chosen from the couplers used conventionally in oxidation dyeing, and among which mention may be made in particular of meta-phenylenediamines, meta-aminophenols, meta-diphenols and heterocyclic couplers such as, for example, indole derivatives, indoline derivatives, and the addition salts thereof with an acid.

These couplers can be chosen in particular from 2-methyl-5-aminophenol, 5-N-β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4- diaminophenoxy)propane, sesamol, α-naphthol, 6-hydroxyindole, 4-hydroxyindole, 4-hydroxy-N-methylindole and 6-hydroxyindoline, and the addition salts thereof with an acid.

When they are present, these additional couplers preferably represent from 0.0005 to 5% by weight approximately relative to the total weight of the dye composition, and even more preferably from 0.005 to 3% by weight approximately relative to this weight.

The addition salts with an acid for the oxidation base(s) and/or for the additional couplers which can be used in the dye composition of the invention are chosen in particular from the hydrochlorides, hydrobromides, sulphates, tartrates, lactates and acetates.

The medium which is suitable for dyeing (or the support) generally consists of water or of a mixture of water and at least one organic solvent for dissolving the compounds which would not be sufficiently water-soluble. As organic solvents, mention may be made, for example, of $C_1$–$C_4$ lower alcohols, such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1% and 40% by weight approximately relative to the total weight of the dye composition, and even more preferably between 5 and 30% by weight approximately.

The pH of the dye composition in accordance with the invention is generally between 3 and 12. It can be adjusted to the desired value using acidifying or basifying agents usually used to dye keratin fibres.

Among the acidifying agents, mention may be made, by way of example, of inorganic or organic acids such as hydrochloric acid, orthophosphoric acid, carboxylic acids such as tartaric acid, citric acid and lactic acid, and sulphonic acids.

Among the basifying agent, mention may be made, by way of example, of aqueous ammonia, alkaline carbonates, alkanolamines such as mono-, di- and triethanolamines and derivatives thereof, sodium hydroxide, potassium hydroxide and the compounds of formula (V) below:

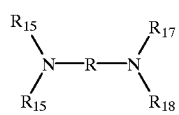

(V)

in which R is a propylene residue optionally substituted with a hydroxyl group or a $C_1$–$C_4$ alkyl radical; $R_{15}$, $R_{16}$, $R_{17}$ and $R_{18}$, which may be identical or different, represent a hydrogen atom or a $C_1$–$C_4$ alkyl or $C_1$–$C_4$ hydroxyalkyl radical.

The dye composition according to the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifiers.

Needless to say, the person skilled in the art will take care to select the optional complementary compound(s) mentioned above, such that the advantageous properties intrinsically associated with the dye composition according to the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The subject of the invention is also the use of the pyrazoline-3,5-diones of formula (I) above, as couplers, in combination with at least one oxidation base for the oxidation dyeing of keratin fibres, and in particular human keratin fibres such as the hair.

Another subject of the invention is a process for the oxidation dyeing of keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition only at the moment of use, or which is present in an oxidizing composition that is applied simultaneously or sequentially in a separate manner.

According to a particularly preferred embodiment of the dyeing process according to the invention, the dye composition described above is mixed, at the moment of use, with an oxidizing composition containing, in a medium which is suitable for dyeing, at least one oxidizing agent that is present in an amount which is sufficient to develop a coloration. The mixture obtained is then applied to the keratin fibres and is left to stand on them for 3 to 50 minutes approximately, preferably 5 to 30 minutes approximately, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that after mixing with the dye composition, the pH of the resulting composition applied to the keratin fibres preferably ranges between 3 and 12 approximately and even more preferably between 5 and 11. It is adjusted to the desired value using acidifying or basifying agents usually used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels or in any other form which is suitable for dyeing keratin fibres, and in particular human hair.

Another subject of the invention is a dyeing "kit" or multi-compartment device or nay other multi-compartment packaging system in which a first compartment contains the dye composition as defined above and a second compartment contains the oxidizing composition as defined above. These devices can be equipped with means which allow the desired mixture to be delivered onto the hair, such as the devices described in patent FR-2,586,913 in the name of the Applicant.

EXAMPLES

Examples 1 and 2 of Dyeing in Alkaline Medium

The following dye compositions, in accordance with the invention, were prepared (contents in grams):

| EXAMPLE | 1 | 2 |
|---|---|---|
| 1,2-Diphenylpyrazoline-3,5-dione (coupler) | 0.756 | — |
| 1,2-Diethylpyrazoline-3,5-dione (coupler) | — | 0.468 |
| Para-phenylenediamine | 0.324 | — |
| 1,3-Dimethyl-4,5-diaminopyrazole dihydrochloride (oxidation base) | — | 0.597 |
| Common dye support | (*) | (*) |
| Demineralized water qs | 100 g | 100 g |

NB: the 1,2-diphenylpyrazoline-3,5-dione and the 1,2-diethylpyrazoline-3,5-dione were prepared according to the synthetic process described in U.S. Pat. No. 4,128,425.

| | |
|---|---|
| Benzyl alcohol | 2.0 g |
| Polyethylene glycol containing 6 mol of ethylene oxide | 3.0 g |
| Ethanol | 20.0 g |
| ($C_8$–$C_{10}$)Alkylpolyglucoside as an aqueous solution containing 60% active material, buffered with ammonium citrate, sold under the name Oramix CG110 by the company SEPPIC | 6.0 g |
| Aqueous ammonia containing 20% $NH_3$ | 10.0 g |
| Sodium metabisulphite | 0.228 g |
| Sequestering agent | qs |

At the moment of use, each dye composition was mixed with an equal weight-amount of an aqueous ammonium persulphate solution at a concentration of $6 \times 10^{-3}$ mol %.

The mixture obtained was applied for 30 minutes to locks of permanent-waved or non-permanent-waved natural grey hair containing 90% white hairs, at a rate of 10 g per 1 g of hair. After rinsing, washing with a standard shampoo and drying, the locks were dyed in the shades featured in the table below:

| Example | pH of the mixture | Shade obtained on natural grey hair containing 90% white hairs | Shade obtained on permanent-waved grey hair containing 90% white hairs |
|---|---|---|---|
| 1 | 9.3 | deep, "washed" iridescent | deep, "washed" iridescent |
| 2 | 9.9 | light saffron-yellow | saffron-yellow |

What is claimed is:

1. A process for the oxidation dyeing of keratin fibers comprising:
   (a) applying at least one dyeing composition to said keratin fibers;
   (b) developing a color at acidic, neutral, or alkaline pH in the presence of an oxidizing agent which is added to said at least one dyeing composition at the time said at least one dyeing composition is applied, or which is present in an oxidizing composition that is applied:
      (i) separately from said at least one dyeing composition at the same time that said at least one dyeing composition is applied to said fibers, or
      (ii) sequentially with said at least one dyeing composition, wherein said at least one dyeing composition comprises, in a medium suitable for dyeing:
   (a) at least one coupler chosen from at least one pyrazoline-3,5-dione compound of formula (I) and acid addition salts thereof;

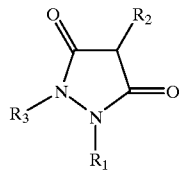

(I)

wherein:
   $R_2$ is chosen from a hydrogen atom; a halogen atom; an acetylamindo group; an alkoxy radical; an acyloxy radical; an aryloxy radical; an arylthio radical; an alkylthio radical; a heteroarylthio radical; a heteroaryloxy radical; a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical, an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinly; a 2-oxy-1,2-dihydro-1-pyridyl radical; an alkylamido; an arylamido; a radical $NR^{III}R^{IV}$ wherein $R^{III}$ and $R^{IV}$ are independently chosen from a $C_1$–$C_4$ alkyl, a hydroxyalkyl; a carboxyl; and an alkoxycarboxyl radical; wherein all of said radicals are substituted or unsubstituted;
   $R_1$ and $R_3$ independently are chosen from a hydrogen atom; a linear or branched $C_1$–$C_5$ alkyl radical; a $C_2$–$C_4$ mono- or polyhydroxyalkyl radical; a $C_2$–$C_4$ aminoalkyl radical; a phenyl radical; a phenyl radical substituted with a halogen atom or a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy or amino radical; and a radical

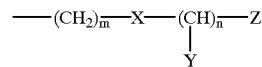

wherein m and n independently are chosen from integers ranging from 1 to 3, X is chosen from an oxygen atom and an NH group, Y is chosen from a hydrogen atom and a methyl radical, and Z is chosen from a methyl radical, a group OR or NRR' wherein R and R' independently are chosen from a hydrogen atom, a methyl radical and an ethyl radical; an amino radical; a $C_1$ –$C_4$ alkylamino; a carboxyl radical; an alkoxycarbonyl radical; an aryloxycarbonyl radical; a 5- or 6-membered heterocycle with at least one nitrogen, sulphur or oxygen atom; an acyl radical; a sulphonyl group; and a phosphonyl group; and wherein when $R_2$ and $R_3$ simultaneously represent a hydrogen atom, then $R_1$ is other than a hydrogen atom, a $C_1$–$C_5$ alkyl radical or phenyl radical; and (b) at least one oxidation base;

wherein said at least one coupler and said at least one oxidation base are present in said composition in an amount effective for dyeing keratin fibers.

2. A process according to claim 1, wherein said keratin fibers are human hair.

3. A process according to claim 1, wherein said at least one dyeing composition is mixed with an oxidation composition in a medium suitable for dyeing at the time of said applying step, wherein said oxidizing composition comprises at least one oxidizing agent present in an amount sufficient to develop coloration.

4. A process according to claim 3, wherein said process further comprises:

waiting for from 3 to 50 minutes after said at least one dyeing composition is applied to keratin fibers;

rinsing said keratin fibers; and washing, rinsing and drying said keratin fibers.

5. A process according to claim 4, wherein said waiting step is carried out for from 5 to 30 minutes.

6. A process according to claim 1, wherein said at least one oxidizing agent is a hydrogen peroxide, urea peroxide, alkali metal bromate, or a persalt.

7. A process according to claim 6, wherein said at least one oxidizing agent is a persalt, and further wherein said persalt is a perborate or persulphate.

8. A process according to claim 6, wherein said at least one oxidizing agent is hydrogen peroxide.

9. A multi-compartment dyeing kit for dyeing keratin fibers comprising a first compartment containing at least one dyeing composition and a second compartment containing at least one oxidizing composition, wherein said at least one dyeing composition comprises, in a medium suitable for dyeing:

(a) at least one coupler chosen from at least one pyrazoline-3,5-dione compound of formula (I) and acid addition salts thereof;

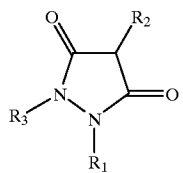

(I)

wherein:

$R_2$ is chosen from a hydrogen atom; a halogen atom; an acetylamido group; an alkoxy radical; an acyloxy radical; an aryloxy radical; an arylthio radical; an alkylthio radical; a heteroarylthio radical; a heteroaryloxy radical; a thiocyano radical; an N,N-diethylthiocarbonylthio radical; a dodecyloxythiocarbionylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical, an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1,2-dihydro-1-pyridyl radical; an alkylamido; an arylamido; a radical $NR^{III}R^{IV}$ wherein $R^{III}$ and $R^{IV}$ are independently chosen from a $C_1$–$C_4$ alkyl, a hydroxyalkyl; a carboxyl; and an alkoxycarboxyl radical; wherein all of said radicals are substituted or unsubstituted;

$R_1$ and $R_3$ independently are chosen from a hydrogen atom; a linear or branched $C_1$–$C_5$ alkyl radical; a $C_2$–$C_4$ mono- or polyhydroxylakyl radical; a $C_2$–$C_4$ aminoalkyl radical; a phenyl radical; a phenyl radical substituted with a halogen atom or a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy or amino radical; and a radical

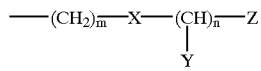

wherein m and n independently are chosen from integers ranging from 1 to 3, X is chosen from an oxygen atom and an NH group, Y is chosen from a hydrogen atom and a methyl radical, and Z is chosen from a methyl radical, a group OR or NRR' wherein R and R' independently are chosen from a hydrogen atom, a methyl radical and an ethyl radical; an amino radical; a $C_1$–$C_4$ alkylamino; a carboxyl radical; an alkoxycarbonyl radical; an aryloxycarbonyl radical; a 5- or 6-membered heterocycle with at least one nitrogen, sulphur or oxygen atom; an acyl radical; a sulphonyl group; and a phosphonyl group; and wherein when $R_2$ and $R_3$ simultaneously represent a hydrogen atom, then $R_1$ is other than a hydrogen atom, a $C_1$–$C_5$ alkyl radical or a phenyl radical; and (b) at least one oxidation base;

wherein said at least one coupler and said at least one oxidation base are present in said composition in an amount effective for dyeing keratin fibers.

* * * * *

UNITED STATES PATENT AND TRADEMARK OFFICE
CERTIFICATE OF CORRECTION

PATENT NO. : 6,210,447 B1
DATED : April 3, 2001
INVENTOR(S) : Vidal et al.

Page 1 of 1

It is certified that error appears in the above-identified patent and that said Letters Patent is hereby corrected as shown below:

<u>Title page,</u>
Item [75], line 1, change "Gërard" to -- Gérard --;

<u>Claim 1, column 10,</u>
Line 18, change "acetylamindo" to -- acetylamido --;
Line 30, change "oxazolidinly" to -- oxazolidinyl --;

<u>Claim 9, column 11,</u>
Line 37, change "thereof;" to -- thereof: --; and

<u>Claim 9, column 12,</u>
Lines 1-2, change "dodecyloxythiocarbionylthio" to -- dodecyloxythiocarbonylthio --.

Signed and Sealed this

Sixteenth Day of October, 2001

Attest:

NICHOLAS P. GODICI
Attesting Officer
Acting Director of the United States Patent and Trademark Office